United States Patent [19]

Ollar et al.

[11] Patent Number: 5,750,363
[45] Date of Patent: May 12, 1998

[54] METHOD FOR DETERMINING THE ANTIMICROBIAL AGENT SENSITIVITY OF A NONPARAFFINOPHILIC MICROORGANISM AND AN ASSOCIATED APPARATUS

[75] Inventors: Robert-A. Ollar, Milford; Mitchell S. Felder, Hermitage, both of Pa.

[73] Assignee: Infectech, Inc., Sharon, Pa.

[21] Appl. No.: 858,131

[22] Filed: May 19, 1997

Related U.S. Application Data

[63] Continuation-in-part of Ser. No. 528,192, Sep. 14, 1995, Pat. No. 5,663,056.

[51] Int. Cl.$^6$ .............................. C12Q 1/02; C12Q 1/24; C12Q 1/18; C12Q 1/14
[52] U.S. Cl. .................. 435/29; 435/30; 435/32; 435/36; 435/42; 435/34; 435/4; 435/852; 435/848; 435/849; 435/879; 435/885; 435/882; 435/883; 435/283.1; 435/287.1; 422/50; 422/68.1
[58] Field of Search .................. 435/29, 30, 32, 435/36, 42, 34, 4, 852, 848, 849, 879, 885, 882, 883, 283.1, 287.1; 422/50, 68.1

[56] References Cited

U.S. PATENT DOCUMENTS

| | | | |
|---|---|---|---|
| 3,826,717 | 7/1974 | Gilbert et al. | 435/29 |
| 4,683,195 | 7/1987 | Mullis et al. | 435/29 |
| 4,683,201 | 7/1987 | Hamill et al. | 435/29 |
| 4,683,202 | 7/1987 | Mullis | 435/29 |
| 4,692,407 | 9/1987 | Jordan et al. | 435/29 |
| 4,782,025 | 11/1988 | Inoue et al. | 435/29 |
| 5,153,119 | 10/1992 | Ollar | 435/29 |
| 5,316,918 | 5/1994 | Ollar | 435/29 |

OTHER PUBLICATIONS

Wallace, J.M. et al., "*Mycobacterium avium* Complex Infection In Patients With The Acquired Immunodeficiency Syndrome* A Clinicopathologic Study", *Chest*, 93 (5), pp. 926–932 (1988). Month not available.

Wolinsky, E., "Nontuberculous Mycobacteria And Associated Diseases", *American Review of Respiratory Disease*, vol. 119: 107–159 (1979). Month not available.

Horsburgh, C.R., Jr. et al., "Disseminated Infection with *Mycobacterium avium–intracellulare*", *Medicine*, vol. 64, No. 1: 36–48 (1983). Month not available.

Horsburgh, C.R., Jr. et al., "The Epidemiology Of Disseminated Nontuberculous Mycobacterial Infection In The Acquired Immunodeficiency Syndrome (AIDS)", *American Review of Respiratory Disease*, 139: 4–7 (1989). Month not available.

Reichert, C.M. et al., "Pathologic Features Of Aids", *Aids: Etiology, Diagnosis, Treatment and Prevention*, pp. 111 and 134, J.B. Lippincott Company (1985). Month not available.

Hawkins, C.C. et al., "*Mycobacterium avium* Complex Infections In Patients With The Acquired Immunodeficiency Syndrome", *Annals of Internal Medicine*, 105: 184–188 (1986). Month not available.

(List continued on next page.)

*Primary Examiner*—Louise N. Leary
*Attorney, Agent, or Firm*—David V. Radack; Eckert Seamans Cherin & Mellott, LLC

[57] ABSTRACT

A method for determining the sensitivity of at least one nonparaffinophilic microorganism from a specimen obtained from a patient to an antimicrobial agent. The method includes providing at least one receptacle containing an aqueous solution that does not contain a carbon source and inoculating the solution with the specimen. The method further includes placing into the receptacle (i) a slide having bound thereto a carbon source and (ii) a predetermined quantity of an antimicrobial agent to be tested. By observing the nonparaffinophilic microorganism growth or lack thereof on the slide, it can be determined whether the predetermined quantity of the antimicrobial agent is effective in inhibiting growth of the nonparaffinophilic microorganism on the slide. An associated apparatus is also disclosed.

36 Claims, 1 Drawing Sheet

OTHER PUBLICATIONS

Hoy, J. et al, "Quadruple–Drug Therapy For *Mycobacterium avium–intracellulare* Bacteremia In AIDS Patients", *The Journal of Infectious Diseases*, 161: 801–805 (Apr. 1990).

Fuhs, G.W., "Der Mikrobielle Abbau Von Kohlenwasserstoffen", *Arch. Mikrobiol.*, 39:374–422 (1961). Month not available.

Mishra, S.K. et al., "Observations On Paraffin Baiting As A Laboratory Diagnostic Procedure In Nocardiosis", *Mycopathologica and Mycologia Applicatia*, vol. 51, 2–3, pp. 147–157 (1973). Month not available.

Ollar. R.–A., "A Paraffin Baiting Technique That Enables A Direct Microscopic View Of in situ Morphology Of *Nocardia asteroides* With The Acid–Fast Or Fluorescence Staining Process", *Zbl. Bakt. Hyg., I. Abt. Orig. A 234*, pp. 81–90 (1976). Month not available.

Kemper, C.A. et al., "Microbiologic And Clinical Response Of Patients With AIDS and MAC Bacteremia To A Four Oral Drug Regimen", *American Society For Microbiology*, (Abstract), p. 297 (1990). Month not available.

Klatt, E.C. et al., "Pathology Of *Myobacterium avium–intracellulare* Infection In Acquired Immunodeficiency Syndrome", *Human Pathology*, vol. 18, No. 7: 709–714 (Jul. 1987).

Bermudez, L.E. et al., "An Animal Of *Mycobacterium avium* Complex Disseminated Infection After Colonization Of The Intestinal Tract", *The Journal of Infectious Diseases*, 165: 75–79 (Jan. 1992).

Murphey, S.A. et al., "*Mycobacterium avium–intracellulare* In A Hospital Hot Water System: Epidemiologic Investigation", *American Society For Microbiology*, 277 (1983). Month not available.

Ma, P. et al., "Definitive Diagnostic Methods For Diseases Indicative Of AIDS", *Aids and Infections of Homosexual Men*, Second Edition, pp. 233–234 Butterworth Publishers (1989). Month not available.

Havlik, J.A., Jr. et al., "Disseminated *Mycobacterium avium* Complex Infection: Clinical Identification And Epidemiologic Trends", *The Journal of Infectious Diseases*, 165: 577–580 (Mar. 1992).

Inderlied, C.B. et al., "Disseminated *Mycobacterium avium* Complex Infection", *Aids Clinical Review*, pp. 165–191 (1990). Month not available.

Gonzalez, R. et al., "Evaluation Of Gen–Probe DNA Hybridization Systems For The Identification Of *Mycobacterium tuberculosis* And *Mycobacterium avium–intracellulare*", *Diagn. Microbiol. Infect. Dis.*, 8: 69–77 (1987). Month not available.

Ollar, R.–A. et al., "The Use Of Paraffin Wax Metabolism In The Speciation Of *Mycobacterium avium–intracellulare*", *Tubercle*, 71, pp. 23–28, Longman Group UK, Ltd. (1990). Month not available.

Kemper, C.A. et al., "Treatment Of *Mycobacterium avium* Complex Bacteremia In AIDS With A Four–Drug Oral Regimen", *Annals of Internal Medicine*, 116, No. 6: 466–472 (Mar. 1992).

Heifets, L. et al., "Comparison Of Bactericidal Activities Of Streptomycin, Amikacin, Kanamycin, And Capreomycin Against *Mycobacterium avium* And *Mycobacterium tuberculosis*", *Antimicrobial Agents and Chemotherapy*, pp. 1298–1301 (Aug. 1989).

Hurley, S.S. et al., "Development Of A Diagnostic Test For Johne's Disease Using A DNA Hybridization Probe", *Journal of Clinical Microbiology*, pp. 1582–1587 (Jul. 1989).

Kirihara, J.M. et al., "Improved Detection Times For *Mycobacterium avium* Complex And *Mycobacterium tuberculosis* With The BACTEC Radiometric System", *Journal of Clinical Microbiology*, pp. 841–845 (Nov. 1985).

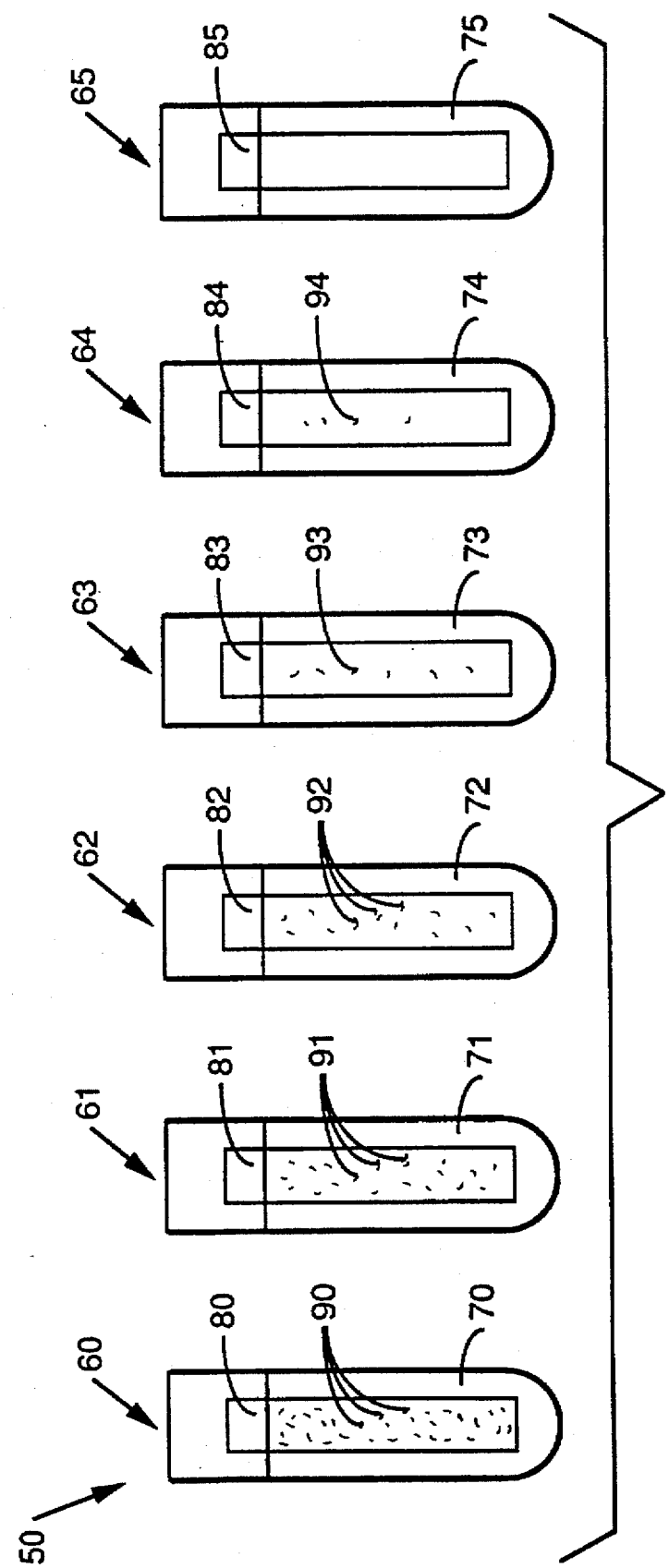

METHOD FOR DETERMINING THE ANTIMICROBIAL AGENT SENSITIVITY OF A NONPARAFFINOPHILIC MICROORGANISM AND AN ASSOCIATED APPARATUS

CROSS-REFERENCE TO RELATED APPLICATION

This is a continuation-in-part of U.S. patent application Ser. No. 08/528,192 filed Sep. 14, 1995 now U.S. Pat. No. 5,663,056.

BACKGROUND OF THE INVENTION

This invention relates to a method for determining the antimicrobial agent sensitivity of a nonparaffinophilic microorganism and an associated apparatus.

Treating infections very often involves educated guesses by medical personnel as to the nature of the microorganism involved and the correct antimicrobial agent and quantity thereof needed to effectively treat the microorganism present in the infected tissue. Often times, there is a need to treat a mixed flora of several microorganisms. Medical personnel are acutely interested in rapidly ascertaining which antimicrobial agents, and which dosages, are necessary in order to assure effective inhibition of the growth of all microorganisms present in the patient.

There is presently no effective, efficient and economical way for a physician to rapidly ascertain which antimicrobial agent, and which dosage is necessary in order to treat the patient. A physician simply does not have available to him or her the type of information regarding antimicrobial agent sensitivity that would make a more exact selection of an antimicrobial agent possible and, once an appropriate antimicrobial agent is selected, facilitate a more precise dosage for treatment. If this information was available, a physician could more effectively treat the infection. Furthermore, because some antimicrobial agents are expensive, the information could be used so that only that amount of antimicrobial agent needed could be used to treat the infection. Finally, and most importantly, as antimicrobial agents can have undesired side effects, the information can be used to find the most effective antimicrobial agent and dosage thereof, which will limit the undesired side effects.

As used herein, the term "nonparaffinophilic microorganism" means any microorganism sustained by a carbon source other than paraffin. Examples of such nonparaffinophilic microorganisms include, but are not limited to, the following: *Mycobacterium tuberculosis; Mycobacterium paratuberculosis; Mycobacterium leprae*; Staphylococcus; Streptococcus; *E. coli*; Listeria; Brucellae; Humemophilus; Treponema; Pneumococcus; Clostridium; Cryptococcus; Coccidioides; Histoplasma; *Klebsiella pneumoniae*; Shigella spp.; Salmonella spp.; Salmonella; *E. coli* (0157); and *Helicobacter pylori*. Also, as used herein, the term "patient" refers to a member of the animal kingdom, including human beings, whose body specimen is being processed by the method and apparatus of the invention.

U.S. Pat. Nos. 5,153,119 and 5,316,918 disclose methods and apparatus for identifying and testing the antibiotic sensitivity of *Mycobacterium avium-intracellulare* ("MAI"), a paraffinophilic microorganism. The inventor named on those patents is Robert-A. Ollar, one of the co-inventors of the invention disclosed herein. This method involves providing a receptacle containing an aqueous solution and inoculating into the solution a specimen. After this, a paraffin coated slide is placed into the receptacle. The slide is then observed for the presence or absence of growth of MAI.

Despite the existence of Dr. Ollar's patents, there still remains a need for a method of testing the antimicrobial agent sensitivity of one or more nonparaffinophilic microorganisms in a way that maximizes the efficacy of the antimicrobial agent used to inhibit growth of the one or more nonparaffinophilic microorganisms that may be present in a patient.

SUMMARY OF THE INVENTION

The invention has met or exceeded the above-mentioned need as well as others. The method for determining the sensitivity of a nonparaffinophilic microorganism from a specimen obtained from a patient to an antimicrobial agent comprises providing at least one receptacle containing an aqueous solution that does not contain a carbon source and inoculating the solution with the specimen. The method further includes placing into the receptacle (i) a slide having bound thereto a carbon source and (ii) a predetermined quantity of an antimicrobial agent. By observing the nonparaffinophilic microorganism growth or lack thereof on the slide, it can be determined whether the predetermined quantity of the antimicrobial agent is effective in inhibiting growth of the nonparaffinophilic microorganism on the slide.

An associated apparatus is also disclosed. The apparatus comprises a receptacle adapted to contain an aqueous solution that does not contain a carbon source, an amount of antimicrobial agent to be tested and the specimen. The apparatus further includes a slide having bound thereto a carbon source, the slide being adapted to being placed in the receptacle. Again, observation of the growth of the nonparaffinophilic microorganism from the specimen on the slide can be used to determine the concentration of the antimicrobial agent necessary to resist the nonparaffinophilic microorganism growth on the slide.

BRIEF DESCRIPTION OF THE DRAWING

A full understanding of the invention can be gained from the following detailed description of the invention when read in conjunction with the accompanying lone drawing which shows one embodiment of the antimicrobial agent sensitivity apparatus.

DETAILED DESCRIPTION

The method and apparatus of the invention provide an efficient, effective and economical way of determining the sensitivity of at least one nonparaffinophilic microorganism to different antimicrobial agents and predetermined quantities thereof. Referring now to the lone Figure, the antimicrobial agent sensitivity method will be explained with reference to one embodiment of the antimicrobial agent sensitivity apparatus 50. The apparatus 50 consists of six receptacles in the form of test tubes 60, 61, 62, 63, 64, 65 each containing an amount of an aqueous solution, such as Czapek broth 70, 71, 72, 73, 74, 75. It will be appreciated that the aqueous solution should not contain any carbon source, as it is desired to provide a sole carbon source on the slide (discussed below) in order to effectively grow the nonparaffinophilic microorganism to be tested on the slide and not in the aqueous solution. The aqueous solutions in test tubes 61–65, preferably but not necessarily, contain uniform intervals of increasing concentrations of an antimicrobial agent to be tested. Test tube 60 is used as a control tube that does not contain any antimicrobial agent.

The specimen from the patient is then inoculated into each of the test tubes 60–65. The specimen can be a blood sample; any biopsy or tissue specimen; stomach fluid; urine; cerebral spinal fluid; nasopharyngeal mucosa or saliva. These specimens can be obtained from the patient in the doctor's office or in the emergency room of a hospital, for example, by known techniques.

Slides 80, 81, 82, 83, 84 and 85 with a carbon source bound thereto are then placed into respective test tubes 60, 61, 62, 63, 64 and 65. The slides are incubated for a period of a minimum of twenty-four (24) hours. By observing nonparaffinophilic microorganism growth 90, 91, 92, 93, 94 on the slides 80–85, the minimum inhibitory concentration ("MIC") of the antimicrobial agent necessary to prevent nonparaffinophilic microorganism growth can be determined. In this case, slide 85 has no nonparaffinophilic microorganism growth, thus the MIC concentration is found in test tube 75. Once the MIC is found, a competent physician can use conventional physiological methodologies to determine a proper dosage for the particular patient.

It will be appreciated that a specimen can sometimes have more than one nonparaffinophilic microorganisms present therein. For example, if a patient has a brain abscess associated with a bacterial endocarditis, the patient will most likely have a single pathogen (i.e., staphylococcus). However, there may be a mixed flora which has grown on the slide (i.e., staphylococcus and meningococci). It is imperative, however, to treat all bacterial flora, as any bacteria present are causing pathogenicity in the patient. This invention allows a physician to specify an antimicrobial agent and a particular dosage thereof which will inhibit all flora growing on the slide, and which is thus effective in treating all nonparaffinophilic microorganisms which are causing pathogenicity in the patient.

It will be appreciated that although apparatus 50 is shown with multiple receptacles and multiple slides 80–85, that the invention is not limited to multiple receptacles and multiple slides, but covers also a single receptacle and a single slide.

The carbon source and the slides 80–85 can include a gelatinous matrix containing a carbon source. A carbon source can be one or more of those selected from the group consisting of glucose, fructose, glycerol, mannitol, asparagine, casein, adonitol, 1-arabinose, cellobiose, dextrose, dulcitol, d-galactose, inositol, inulin, lactose, levulose (d-fructose), maltose, d-mannitol, d-mannose, melibiose, raffinose, rhamnose, sucrose, salicin, d-sorbitol, trehalose and d-xylose, among others. Another embodiment can include providing a slide and coating the slide with an adhesive and securing a plurality of gel beads to the adhesive. The carbon source can then be either ionically or affinity bound to the gel beads.

The slides 80–85 with the gelatinous matrix containing a carbon source can be prepared by the following method. A receptacle, such as a laboratory beaker, is first filled with 100 ml of distilled water. Into the beaker is placed two (2) grams of agar (the gelatinous matrix) and three (3) grams of a carbon source (such as glucose). This mixture is then boiled and steam sterilized and the molten gelatinous matrix with a carbon source is poured into a petri dish, which is sitting on a hot plate. In this way the gelatinous matrix/carbon source remains molten. After this, a sterile slide such as slide 80 is dropped into the molten gelatinous matrix/carbon source and becomes coated therewith. The now coated slide is removed from the petri dish and allowed to stand for a minute or two in order to solidify the coating thereon. The slide with the coating of a gelatinous matrix containing a carbon source is then ready to be placed in one of the test tubes 60–65 containing the aqueous solution and the specimen.

An alternative method of preparing the slide involves first coating the slide with an adhesive, such as collodion and then applying a plurality of gel beads (commercially available from Pharmacia of Parsippany, New Jersey) to the adhesive. The gel beads are approximately one micron in diameter. The slide containing the coating of gel beads is now immersed in a buffering agent containing the carbon source (such as glucose) to attach the carbon source to the gel beads either ionically or affinity-wise.

Nonparaffinophilic microorganisms that can be identified using the method of the invention include any microorganism sustained by a carbon source other than paraffin. Nonparaffinophilic microorganisms include, but are not limited to, *Mycobacterium tuberculosis; Mycobacterium paratuberculosis; Mycobacterium leprae*; Staphylococcus; Streptococcus; *E. coli*; Listeria; Brucellae; Humemophilus; Treponema; Pneumococcus; Clostridium; Cryptococcus; Coccidioides; Histoplasma; *Klebsiella pneumoniae*; Shigella spp.; Salmonella spp.; Salmonella; *E. coli* (0157); and *Helicobacter pylori*.

In order to further elucidate the invention, the following examples will be provided.

EXAMPLE 1

It is desired to determine the proper antimicrobial agent dosage to give to a patient having *Klebsiella pneumoniae*. Several receptacles are prepared, each having therein an aqueous solution that does not contain a carbon source including

| Distilled Water | 1 liter |
| Beef Extract | 1 gram |
| Peptone | 10 grams |
| NaCl | 5 grams |
| Phenol Red | 0.018 grams. |

Into each receptacle, except one which will contain no antimicrobial agent and which will act as a viability check, a different amount (preferably in increasing concentrations) of an antimicrobial agent effective against Klebsiella pneumoniae is introduced. After this, an inoculum of the *Klebsiella pneumoniae* is added to each of the receptacles. Finally, a single slide having bound thereto a carbon source such as adonitol, cellobiose, dulcitol, inositol, raffinose, sucrose or salicin is placed into each receptacle. By observing the growth (or lack thereof) on each slide, the proper concentration of the antimicrobial agent needed to inhibit *Klebsiella pneumoniae* growth (also known as the "minimum inhibitory concentration" or "MIC") can be determined. Once this is determined, a competent physician can use conventional physiological methodologies to determine a proper dosage for this particular patient.

EXAMPLE 2

It is desired to determine the proper antimicrobial agent dosage to give to a patient having *E. coli*. Several receptacles are prepared, each having therein an aqueous solution that does not contain a carbon source including

| Distilled Water | 1 liter |
| Beef Extract | 1 gram |
| Peptone | 10 grams |
| NaCl | 5 grams |
| Phenol Red | 0.018 grams. |

Into each receptacle, except one which will contain no antimicrobial agent and which will act as a viability check, a different amount (preferably in increasing concentrations) of an antimicrobial agent effective against *E. coli* is introduced. After this, an inoculum of the *E. coli* is added to each of the receptacles. Finally, a single slide having bound thereto a carbon source such as 1-arabinose, lactose or trehalose is placed into each receptacle. By observing the growth (or lack thereof) on each slide, the proper concentration of the antimicrobial agent needed to inhibit *E. coli* growth (also known as the "minimum inhibitory concentration" or "MIC") can be determined. Once this is determined, a competent physician can use conventional physiological methodologies to determine a proper dosage for this particular patient.

EXAMPLE 3

It is desired to determine the proper antimicrobial agent dosage to give to a patient having *Salmonella typhimurium*. Several receptacles are prepared, each having therein an aqueous solution that does not contain a carbon source including

| Distilled Water | 1 liter |
|---|---|
| Beef Extract | 1 gram |
| Peptone | 10 grams |
| NaCl | 5 grams |
| Phenol Red | 0.018 grams. |

Into each receptacle, except one which will contain no antimicrobial agent and which will act as a viability check, a different amount (preferably in increasing concentrations) of an antimicrobial agent effective against *Salmonella typhimurium* is introduced. After this, an inoculum of the *Salmonella typhimurium* is added to each of the receptacles. Finally, a single slide having bound thereto a carbon source such as dextrose, melibiose or d-xylose is placed into each receptacle. By observing the growth (or lack thereof) on each slide, the proper concentration of the antimicrobial agent needed to inhibit *Salmonella typhimurium* growth (also known as the "minimum inhibitory concentration" or "MIC") can be determined. Once this is determined, a competent physician can use conventional physiological methodologies to determine a proper dosage for this particular patient.

EXAMPLE 4

It is desired to determine the proper antimicrobial agent dosage to give to a patient having *Salmonella arizonae*. Several receptacles are prepared, each having therein an aqueous solution that does not contain a carbon source including

| Distilled Water | 1 liter |
|---|---|
| Beef Extract | 1 gram |
| Peptone | 10 grams |
| NaCl | 5 grams |
| Phenol Red | 0.018 grams. |

Into each receptacle, except one which will contain no antimicrobial agent and which will act as a viability check, a different amount (preferably in increasing concentrations) of an antimicrobial agent effective against *Salmonella arizonae* is introduced. After this, an inoculum of the *Salmonella arizonae* is added to each of the receptacles. Finally, a single slide having bound thereto a carbon source such as d-galactose, d-mannose, rhamnose or d-sorbitol is placed into each receptacle. By observing the growth (or lack thereof) on each slide, the proper concentration of the antimicrobial agent needed to inhibit *Salmonella arizonae* growth (also known as the "minimum inhibitory concentration" or "MIC") can be determined. Once this is determined, a competent physician can use conventional physiological methodologies to determine a proper dosage for this particular patient.

EXAMPLE 5

It is desired to determine the proper antimicrobial agent dosage to give to a patient having *Streptococcus pneumoniae*. Several receptacles are prepared, each having therein an aqueous solution that does not contain a carbon source including

| Distilled Water | 1 liter |
|---|---|
| Beef Extract | 1 gram |
| Peptone | 10 grams |
| NaCl | 5 grams |
| Phenol Red | 0.018 grams. |

Into each receptacle, except one which will contain no antimicrobial agent and which will act as a viability check, a different amount (preferably in increasing concentrations) of an antimicrobial agent effective against *Streptococcus pneumoniae* is introduced. After this, an inoculum of the *Streptococcus pneumoniae* is added to each of the receptacles. Finally, a single slide having bound thereto a carbon source such as inulin or levulose (d-fructose) is placed into each receptacle. By observing the growth (or lack thereof) on each slide, the proper concentration of the antimicrobial agent needed to inhibit *Streptococcus pneumoniae* growth (also known as the "minimum inhibitory concentration" or "MIC") can be determined. Once this is determined, a competent physician can use conventional physiological methodologies to determine a proper dosage for this particular patient.

EXAMPLE 6

It is desired to determine the proper antimicrobial agent dosage to give to a patient having *Staphylococcus aureus*. Several receptacles are prepared, each having therein an aqueous solution that does not contain a carbon source including

| Distilled Water | 1 liter |
|---|---|
| Beef Extract | 1 gram |
| Peptone | 10 grams |
| NaCl | 5 grams |
| Phenol Red | 0.018 grams. |

Into each receptacle, except one which will contain no antimicrobial agent and which will act as a viability check, a different amount (preferably in increasing concentrations) of an antimicrobial agent effective against *Staphylococcus aureus* is introduced. After this, an inoculum of the *Staphylococcus aureus* is added to each of the receptacles. Finally, a single slide having bound thereto a carbon source such as d-mannitol is placed into each receptacle. By observing the growth (or lack thereof) on each slide, the proper concentration of the antimicrobial agent needed to inhibit *Staphylococcus aureus* growth (also known as the "minimum inhibitory concentration" or "MIC") can be determined. Once this is determined, a competent physician can use conventional physiological methodologies to determine a proper dosage for this particular patient.

It will be appreciated that a method of determining the sensitivity of at least one nonparaffinophilic microorganism in a specimen and an associated apparatus has been disclosed. The method is effective and efficient and does not involve the use of expensive and complicated equipment. An associated apparatus is also disclosed.

While specific embodiments of the invention have been disclosed, it will be appreciated by those skilled in the art that various modifications and alterations to those details could be developed in light of the overall teachings of the disclosure. Accordingly, the particular arrangements disclosed are meant to be illustrative only and not limiting as to the scope of the invention which is to be given the full breadth of the appended claims and any and all equivalents thereof.

What is claimed is:

1. A method for determining the antibiotic sensitivity of a nonparaffinophilic microorganism from a specimen obtained from a patient to an antimicrobial agent, said method comprising:

provided a receptacle containing an aqueous solution that does not contain a carbon source;

inoculating said solution with said specimen;

placing into said receptacle (i) a slide having bound thereto a carbon source and (ii) a predetermined quantity of an antimicrobial agent; and observing nonparaffinophilic microorganism growth or lack thereof on said slide to determine whether said predetermined quantity of said antimicrobial agent is effective in inhibiting growth of said nonparaffinophilic microorganism on said slide.

2. The method of claim 1, including determining the antibiotic sensitivity of *Klebsiella pneumoniae* by using as said carbon source one selected from the group consisting of adonitol, cellobiose, dulcitol, inositol, raffinose, sucrose and salicin.

3. The method of claim 1, including determining the antibiotic sensitivity of *E. coli* by using as said carbon source one selected from the group consisting of l-arabinose, lactose and trehalose.

4. The method of claim 1, including determining the antibiotic sensitivity of *Salmonella typhimurium* by using as said carbon source one selected from the group consisting of dextrose, melibiose and d-xylose.

5. The method of claim 1, including determining the antibiotic sensitivity of *Salmonella arizonae* by using as said carbon source one selected from the group consisting of d-galactose, d-mannose, rhamnose and d-sorbitol.

6. The method of claim 1, including determining the antibiotic sensitivity of *Streptococcus pneumoniae* by using as said carbon source one selected from the group consisting of inulin and d-fructose.

7. The method of claim 1, including determining the antibiotic sensitivity of *Staphylococcus aureus* by using d-mannitol as said carbon source.

8. The method of claim 1, wherein said aqueous solution includes distilled water, beef extract, peptone, NaCl and phenol red.

9. The method of claim 8, wherein said aqueous solution includes 1 liter distilled water, 1 gram beef extract, 10 grams peptone, 5 grams NaCl and 0.018 grams phenol red.

10. The method of claim 1, including employing as said slide one coated with a gelatinous matrix containing said carbon source.

11. The method of claim 1, including providing said slide by first adhering to said slide a plurality of gel beads and then bonding to said gel beads said carbon source.

12. The method of claim 11, wherein said carbon source is ionically bound to said gel beads.

13. The method of claim 11, wherein said carbon source is affinity bound to said gel beads.

14. The method of claim 11, including adhering said gel beads to said slide by means of an adhesive.

15. The method of claim 14, including employing as said adhesive a gelatinous matrix with said carbon source.

16. The method of claim 1, including employing as said carbon source one or more of the group consisting of glucose, fructose, glycerol, mannitol, asparagine, casein, adonitol, l-arabinose, cellobiose, dextrose, dulcitol, d-galactose, inositol, inulin, lactose, levulose (d-fructose), maltose, d-mannitol, d-mannose, melibiose, raffinose, rhamnose, sucrose, salicin, d-sorbitol, trehalose and d-xylose.

17. The method of claim 1, including employing as said specimen one selected from the group consisting of blood, stomach fluid, urine, cerebral spinal fluid, nasopharyngeal mucosa and saliva.

18. The method of claim 1, including providing a plurality of receptacles each containing an aqueous solution;

inoculating each receptacle with an amount of said specimen;

placing (i) a separate slide coated with a carbon source and (ii) an amount of an antimicrobial agent to be tested in each receptacle, each said receptacle containing a different predetermined quantity of said antimicrobial agent; and observing said nonparaffinophilic microorganism growth or lack thereof on said slides to determine a minimum inhibitory concentration of said antimicrobial agent to inhibit growth of said nonparaffinophilic microorganism.

19. An apparatus for determining the sensitivity of a nonparaffinophilic microorganism from a specimen obtained from a patient to an antimicrobial agent, said apparatus comprising:

a receptacle adapted to contain (i) an aqueous solution that does not contain a carbon source; (ii) an amount of said antimicrobial agent to be tested; and (iii) said specimen; and a slide having bound thereto a carbon source.

20. The apparatus of claim 19, wherein said nonparaffinophilic microorganism is *Klebsiella pneumoniae*; and said carbon source is selected from the group consisting of adonitol, cellobiose, dulcitol, inositol, raffinose, sucrose and salicin.

21. The apparatus of claim 19, wherein said nonparaffinophilic microorganism is *E. coli*; and said carbon source is selected from the group consisting of l-arabinose, lactose and trehalose.

22. The apparatus of claim 19, wherein said nonparaffinophilic microorganism is *Salmonella typhimurium*; and said carbon source is selected from the group consisting of dextrose, melibiose and d-xylose.

23. The apparatus of claim 19, wherein said nonparaffinophilic microorganism is *Salmonella arizonae*; and said carbon source is selected from the group consisting of d-galactose, d-mannose, rhamnose and d-sorbitol.

24. The apparatus of claim 19, wherein said nonparaffinophilic microorganism is *Streptococcus pneumoniae*; and said carbon source is selected from the group consisting of inulin and d-fructose.

25. The apparatus of claim 19, wherein said nonparaffinophilic microorganism is *Staphylococcus aureus*; and said carbon source is d-mannitol.

26. The apparatus of claim 19, including said aqueous solution includes distilled water, beef extract, peptone, NaCl and phenol red.

27. The apparatus of claim 26, wherein said aqueous solution includes 1 liter distilled water, 1 gram beef extract, 10 grams peptone, 5 grams NaCl and 0.018 grams phenol red.

28. The apparatus of claim 19, wherein said slide is coated with a gelatinous matrix containing said carbon source.

29. The apparatus of claim 19, wherein said slide is coated with a plurality of gel beads which have bound thereto said carbon source.

30. The apparatus of claim 29, wherein said carbon source is tonically bound to said gel beads.

31. The apparatus of claim 29, wherein said carbon source is affinity bound to said gel beads.

32. The apparatus of claim 29, wherein said gel beads are adhered to said slide by an adhesive.

33. The apparatus of claim 32, wherein said adhesive is collodion.

34. The apparatus of claim 19, wherein said carbon source is one or more of the group consisting of glucose, fructose, glycerol, mannitol, asparagine, casein, adonitol, l-arabinose, cellobiose, dextrose, dulcitol, d-galactose, inositol, inulin, lactose, levulose (d-fructose), maltose, d-mannitol, d-mannose, melibiose, raffinose, rhamnose, sucrose, salicin, d-sorbitol, trehalose and d-xylose.

35. The apparatus of claim 19, wherein said specimen is one selected from the group consisting of blood, stomach fluid, urine, cerebral spinal fluid, nasopharyngeal mucosa and saliva.

36. The apparatus of claim 19, including a plurality of receptacles each adapted to contain (i) an aqueous solution; (ii) an amount of antimicrobial agent to be tested; and (iii) said specimen; and a plurality of slides each coated with a carbon source, each of which is adapted to being placed in one of said receptacles.

* * * * *